US00RE37393B1

(19) United States
(12) Reissued Patent
Donnelly et al.

(10) Patent Number: US RE37,393 E
(45) Date of Reissued Patent: Sep. 25, 2001

(54) **MUTANT *E. COLI* STRAIN WITH INCREASED SUCCINIC ACID PRODUCTION**

(75) Inventors: Mark Donnelly, Warrenville; Cynthia S. Millard, Plainfield; Lucy Stols, Woodridge, all of IL (US)

(73) Assignee: The University of Chicago, Chicago, IL (US)

(21) Appl. No.: 09/429,693

(22) Filed: Oct. 27, 1999

Related U.S. Patent Documents

Reissue of:
(64) Patent No.: 5,770,435
Issued: Jun. 23, 1998
Appl. No.: 08/556,805
Filed: Nov. 2, 1995

(51) Int. Cl.[7] ..... C12N 1/20; C12P 7/54; C12P 7/46

(52) U.S. Cl. ..... 435/252.33; 435/140; 435/145; 435/252.8; 435/849

(58) Field of Search ..... 435/252.33, 140, 435/145, 252.8, 849

(56) References Cited

U.S. PATENT DOCUMENTS 5,143,834 * 9/1992 Glassner et al. ..... 435/145
5,521,075 * 5/1996 Guettler et al. ..... 435/145
5,573,931 * 11/1996 Guettler et al. ..... 435/145

* cited by examiner

*Primary Examiner*—Herbert J. Lilling
(74) *Attorney, Agent, or Firm*—Cherskov & Flaynik

(57) ABSTRACT

A method for isolating succinic acid producing bacteria is provided comprising increasing the biomass of an organism which lacks the ability to catabolize pyruvate, and then subjecting the biomass to glucose-rich medium in an anaerobic environment to enable pyruvate-catabolizing mutants to grow.

The invention also provides for a mutant that produces high amounts of succinic acid, which has been derived from a parent which lacked the genes for pyruvate formate lyase and lactate dehydrogenase, and which belongs to the E.coli Group of Bacteria.

10 Claims, 2 Drawing Sheets

MUTANT *E. COLI* STRAIN WITH INCREASED SUCCINIC ACID PRODUCTION

Matter enclosed in heavy brackets [ ] appears in the original patent but forms no part of this reissue specification; matter printed in italics indicates the additions made by reissue.

CONTRACTUAL ORIGIN OF THE INVENTION

The United States Government has rights in this invention under Contract No. W-31-109-ENG-38 between the U.S. Department of Energy and the University of Chicago representing Argonne National Laboratory.

BACKGROUND OF THE INVENTION

1. Field of the Invention

This invention relates to a method to produce succinic acid, malic acid or fumaric acid, and more particularly this invention relates to a bacteria that produces high quantities of succinic acid, malic acid and fumaric acid.

2. Background of the Invention

Carboxylic acids hold promise as potential precursors for numerous chemicals. For example, succinic acid can serve as a feedstock for such plastic precursors as 1,4-butanediol (BDO), tetrahydrofuran, and gamma-butyrolactone. New products derived from succinic acid are under constant development, with the most notable of these being polyester which is made by linking succinic acid and BDO. Generally, esters of succinic acids have the potential of being new, "green" solvents that can supplant more harmful solvents and serve as precursors for millions of pounds of chemicals annually at a total market value of over $1 billion. Along with succinic acid, other 4-carbon dicarboxylic acids, such as malic acid, and fumaric acid also have feedstock potential.

The production of these carboxylic acids from renewable feedstocks (in this case through fermentation processes) is an avenue to supplant the more energy intensive methods of deriving such acids from nonrenewable sources. Succinate is an intermediate for anaerobic fermentations by propionate-producing bacteria but those processes result in low yields and concentrations.

Anaerobic rumen bacteria, such as Bacteroides ruminicola and Bacteroides amylophilus also produce succinate. However, rumen organisms are characteristically unstable in fermentation processes.

It has long been known that a mixture of acids are produced from E.coli fermentation, as elaborated in Stokes, J. L. 1949 "Fermentation of glucose by suspensions of Escherichia coli" J. Bacteriol. 5 7:147–158. However, for each mole of glucose fermented, only 1.2 moles of formic acid, 0.1–0.2 moles of lactic acid, and 0.3–0.4 moles of succinic acid are produced. As such, efforts to produce carboxylic acids fermentatively have resulted in relatively large amounts of growth substrates, such as glucose, not being converted to desired product.

Some bacteria, such as A. succiniciproducens, utilized in fermentation processes as outlined in U.S. Pat. No. 5,143,834 to Glassner et al., naturally produce succinic acid in moderate yields. However, this host organism converts at most 1 mole of carbohydrate to 1.33 moles of succinate and 0.67 moles of acetate. Production of the acetate co-product illustrates that one-third of the expensive glucose is not converted to succinate. Furthermore, the A. succiniciproducens host strain has been shown to be not highly osmotolerant in that it does not tolerate high concentrations of salts and is further inhibited by moderate concentrations of product. Lastly, A. succiniciproducens presents handling problems in that as an obligate anaerobe, procedures using the organism must be done in the absence of oxygen. Also, medium preparation for the inoculum requires the addition of tryptophan and also requires the mixing of four different solutions, one of which contains corrosive and toxic $H_2S$.

A need exists in the art for a fermentation process to economically produce high amounts of carboxylic acids, such as succinic acid, malic acid and fumaric acid. The process should utilize low cost nutrients and substrates yet provide for high fermentation rates. To effect such a process, an osmotolerant, well-characterized facultative bacterial host is required to yield desired product in up to a 2:1 molar ratio of product-to-growth substrate.

SUMMARY OF THE INVENTION

It is an object of the present invention to provide a method for producing 4-carbon dicarboxylic acids that overcome many of the disadvantages of the prior art.

Yet another object of the present invention is to provide a strain of a facultative organism which produces concentrations of malic acid in the range of 100 grams per liter. A feature of the invention is the combination of a bacterium, which does not metabolize pyruvate to malic acid, with a malic enzyme gene. An advantage of the invention is the exclusive production of malic acid, or the production of malic acid and succinic acid.

Still another object of the present invention is to provide a strain of a facultative organism which produces succinic acid in a ratio of approximately 2:1 succinic to carbohydrate food source. A feature of the invention is the emergence of the strain after selective culturing techniques. An advantage of the invention is the economical production of succinic acid-producing mutants without the need for time consuming genetic manipulations of parent strains.

Briefly, a method for isolating succinic acid producing bacteria is provided comprising isolating a facultative organism lacking the capacity to catabolize pyruvate; increasing the biomass of the organism in an aerobic process; subjecting the biomass to glucose-rich medium in an anaerobic environment to enable pyruvate-catabolizing mutants to grow; and isolating the mutants.

The invention also provides for a mutant characterized in that it produces a mixture of succinic acid, acetic acid and ethanol as fermentation products, which as been derived from a parent which lacked the genes for pyruvate formate lyase and lactate dehydrogenase, and which belongs to the E. coli Group of Bacteria. On Aug. 20, 1997, this E. coli mutant was placed with the American Type Culture Collection as deposit #202021 and is designated herein as AFP 111. The ATCC is located at 12301 Parklawn Drive, Rockville, Md. 20852.

BRIEF DESCRIPTION OF THE DRAWING

The present invention together with the above and other objects and advantages may best be understood from the following detailed description of the embodiment of the invention illustrated in the drawings, wherein.

DETAILED DESCRIPTION OF THE INVENTION

Figure 1:
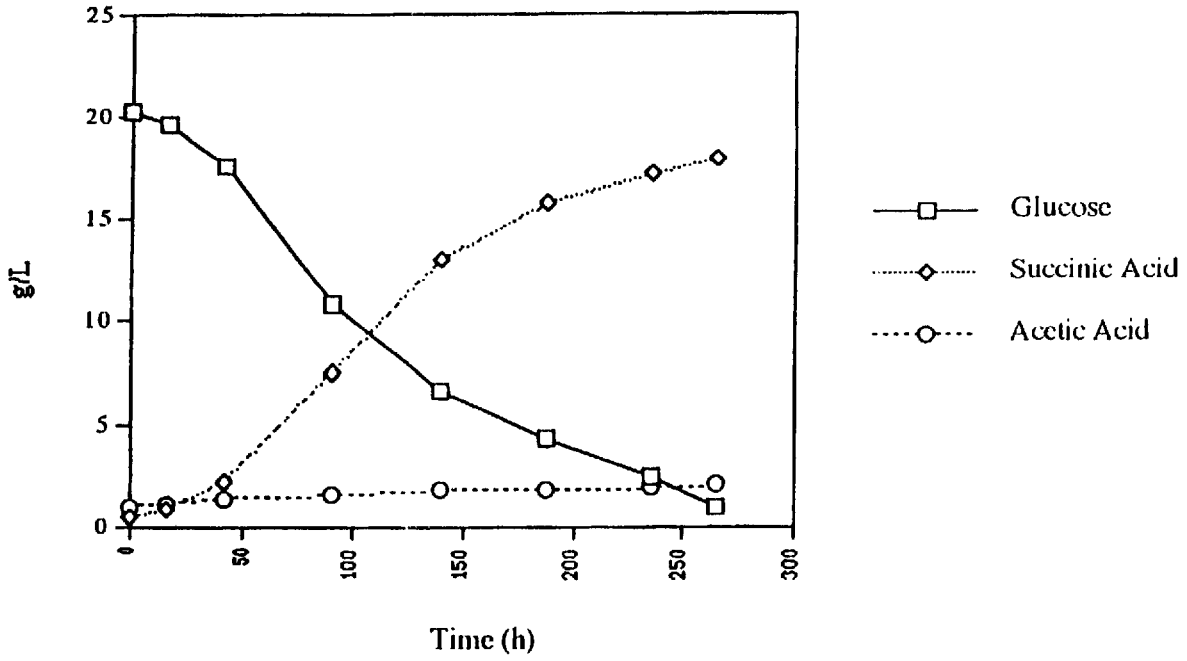
FIG. 1 is a graph depicting an enhanced ratio of succinic acid to acetic acid production, in accordance with the present invention.

Generally, the inventors have found a method for determining bacteria which can economically produce high quantities of succinic acid, fumaric acid and malic acid in fermentation processes. E.coli Mutation Detail In one embodiment, a new mutant strain of E. coli has been developed that will produce increased amounts of succinic acid. The inventors have labeled this strain AFP 111, in as much as the strain has resulted from the efforts of the Alternative Feedstocks Program of the U.S. Department of Energy.

As noted supra, normally, under anaerobic conditions, wild type E. coli produces a mixture of fermentation products, of which succinic acid is a minor component. However, when AFP 111 is grown under anaerobic conditions, the major metabolic product is succinic acid. AFP 111 contains a unique spontaneous chromosomal mutation that produces a mixture of succinic acid, acetic acid and ethanol, with succinic acid as the major product. A maximum yield of 99 percent, weight of succinic acid per weight of glucose is produced with AFP 111. The use of AFP 111 could significantly reduce the cost of producing succinic acid by fermentation processes.

Anaerobic fermentation is the most ancient pathway for obtaining energy from fuels such as glucose. In anaerobic cells it is the sole energy-producing process. In most facultative cells, it is an obligatory first stage in glucose catabolism, which is followed by aerobic oxidation of the fermentation products via the tricarboxylic acid cycle.

The most widely utilized type of fermentation is glycolysis with pyruvate produced as a penultimate product. The disposition of pyruvate depends on which genes are present in the organism. In the presence of lactate dehydrogenase enzyme, glycolysis terminates when pyruvate is reduced via NADH and H+ to lactate. In the presence of pyruvate decarboxylase and alcohol, dehydrogenase, ethanol is formed. In the presence of pyruvate formate lyase, fermentation terminates with the production of acetate, ethanol, and formate, or hydrogen plus carbon dioxide.

If a mutation or a plurality of mutations in a bacterial genome eliminates the genes in that organism responsible for the catabolism of pyruvate, then pyruvate will accumulate. In anaerobically growing E. coli, those genes are pyruvate formate lyase (pfl) and lactate dehydrogenase (Idh). E. coli strain NZN 111, widely available to researchers from Dr. David Clark, Southern Illinois University, Carbondale Ill. 62901, contains mutations in both genes whereby both pfl and Idh have been inactivated due to changes in the E.coli chromosomal DNA sequence. As such, NZN 111 cannot grow fermentatively.

Mutation Procurement Detail

Surprisingly and unexpectedly, the inventors have found that additional changes to NZN 111, occurring either spontaneously either during selective culturing or via plasmid transformation, ultimately result in the emergence of AFP 111 that produces succinic acid as a major product.

Spontaneous chromosomal mutations to NZN 111, which lead to AFP 111-type characteristics, occur when selective environments are utilized in serial culturing techniques. In a first step, NZN 111 biomass is increased aerobically on a rich medium, such as Luria Bertaini (LB) broth (0.5 percent yeast extract, 1 percent tryptone, and 1 percent NaCl, pH 7.5). Yields of between approximately $10^9$ to $10^{10}$ cells per milliliter are desirable. While incubation periods can vary, growth phase durations of between 5–7 hours, at 37° C., and at standard pressure produce the above-mentioned concentrations.

As a second step, the now accumulated biomass is subjected to anaerobic conditions rich in glucose to facilitate growth only of those cells (mutants) able to catabolize pyruvate. Specifically, cells are spread on 1.5 percent Agar plates containing approximately 1 to 30 grams per liter (g/l) of glucose, preferably 10 g/l glucose, and 30 micrograms ($\mu$g) of Kanamycin. The gene for Kanamycin resistance is inserted into the gene for lactate dehydrogenase in NZN 111. Cultures are grown for 24 hours at 37° C., in a controlled anaerobic atmosphere. One anaerobic atmosphere producing good results was a mixture of carbon dioxide and hydrogen, which was provided through the use of an atmosphere control device commercially available from Becton-Dickinson, Cockeysville, Md. as GASPAK™.

The incubation period yielded many colonies of AFP 111 (approximately 2 per $10^7$ cells) and approximately half of those were capable of growing in liquid medium to produce the desired mixture of products.

In the instance of plasmid transformation, when NZN 111 is transformed with the plasmid pMDH13 containing the gene mdh for a mutant malate dehydrogenase enzyme, pyruvate catabolism resumes to produce lactate. Serial culturing of this transformant [NZN 111(pMDH13)] results in AFP 111 containing a spontaneous chromosomal mutation. AFP 111 produces a mixture of succinic acid, acetic acid and ethanol as fermentation products, with succinic acid being produced up to 99 percent by weight compared to the weight of the glucose used in the growth medium. The development and transformation protocol of pMDH 13 is similar to that disclosed in W. E. Boernke, et al. (Sep. 10, 1995) Archives of Biochemistry and Biophysics 322, No. 1 pp. 43–52, incorporated herein by reference.

AFP 111 Growth Detail

The ease of handling of AFP 111 and its subsequent growth make the strain much easier to work with than A. succiniciproducens, which is the state of the art. For example, given the facultative aerobic characteristics of the organism, the invented growth process does not require rigorous use of anaerobic culturing techniques. The process does not require expensive growth medium, such as glucose and tryptophan, to produce a large biomass. Furthermore, the organism is osmotolerant in that it is capable of producing concentrations greater than 50 grams of organic acid salts per liter of fermentation liquor without any inhibition of its metabolism. Finally, AFP 111 bacteria also grow on xylose and other pentose sugars that are not assimilatable by A. succiniciproducens.

For experimental evaluation of the strains described herein, cells are cultured aerobically in glucose-free growth medium (Luria Broth) until cell densities of between 0.5 and 10 $OD_{600}$ are reached.

Once this appropriate biomass of AFP 111 is reached, the cells are then injected or otherwise transferred into a sealed fermentation reaction chamber to be contained therein. The broth is mixed with glucose or some other suitable carbohydrate, such as xylose, galactose or arabinose at concentrations varying between approximately 10 to 30 g/l. The now-contained mixture is subjected to an atmospheric change whereby anaerobic conditions are achieved. One means for achieving the atmospheric change is through a gassing station whereby ambient air is exchanged for carbon dioxide.

Prior to introducing the mixture into the fermentation reaction chamber, the chamber is supplied with an appropriate amount of buffering medium, such as $MgCO_3$, $CaCO_3$, or $CaMg(CO_3)_2$ so as to maintain near neutral pH. Between approximately 4 and 8 weight percent of buffering medium is typically utilized for suitable buffering capacity. Especially good results are obtained when the buffering medium is present as a solid so as to confer a time-release buffering capacity to the fermenting liquor.

The above procedure results in high yields of succinic acid.

For example, a 6:1 ratio of succinic acid to acetic acid by weight was obtained, with a 99 percent yield. The succinic acid to acetic acid ratio increases even further when fermentation is conducted in the presence of hydrogen gas in $H_2$ concentrations of between approximately 25 percent to 100 percent. These results indicate that unlike the state of the art organisms, the invented mutant AFP 111 uses exogenous hydrogen as a reductant. For example, when luria broth, glucose, buffering agent, and a mixture of hydrogen gas and carbon dioxide ($CO_2$ being liberated from the buffering agent) are present, succinic acid to acetic acid ratios approaching 9 are obtained; as depicted in FIG. 1. This result reflects another advantage of the present method of pinpointing the catabolism of glucose to desired product, without unwanted, acetate-producing side reactions.

Table 1 below illustrates the product distribution of the dicarboxylic acids for the original parent W1485 (also available from Southern Illinois University), NZN 111 and AFP 111.

TABLE 1

Product yield in molar yield viz. initial glucose (mole percent) for AFP 111 and ancestors.

| Product | Original Parent W1485 | Immediate Parent NZN 111 | Mutant AFP 111 |
|---|---|---|---|
| Succinic A. | 12 | 2 | 109 |
| Lactic A. | 24 | 0 | 0 |
| Pyruvic A. | 1 | 17 | 0 |
| Formic A. | 26 | 0 | 0 |
| Acetic A. | 1 | 6 | 49 |
| Ethanol | 80 | 15 | 47 |
| Total Product | 193% | 41% | 206%* |

*Molar yield values in theory can be 200 percent because one molecule of glucose can give two of all the products.

When a 100 percent carbon dioxide atmosphere is utilized, succinic acid production is enhanced with concentrations of succinic acid reaching approximately 45 grams per liter, productivity reaching approximately 1.6 grams per liter per hour, percent yield of grams of succinic acid to grams of glucose reaching 99 percent and the weight ratio of succinic acid to acetic acid reaching approximately six.

Succinic acid is also produced when the E. coli NAD-dependent malic enzyme is produced in NZN 111 (by the addition and induction of the gene maeA). In this instance, the inducible plasmid pMEE2-1 is used to allow expression of the malic enzyme gene in the transformant NZN 111 (pMEE2-1).

Genomic DNA isolated from E. coli MC1061 was used as a template for cloning malic enzyme by PCR. The E. coli MC1061 was digested with restriction endonucleases Hind III and Pst I, with the resulting digested material sized on 1 percent TAE agarose gel. The size of the genomic DNA fragment containing the malic enzyme gene was determined using Southern Blot analysis with the PhotoGene Nucleic Acid Detection System (Cat 8192SA), as described supra.

Biotinylated Probe

Preparation Detail

Primers were based on published partial DNA sequence of the gene:

Sense: CGAAGAACAAGCGGAACGAGCAT;

Antisense: GGCAGCAGGTTCGGCATCTTGTC (*SEQ ID NO.2*).

These primers were combined at 1 micromolar ($\mu$M) with approximately 20 nanograms (ng) of genomic DNA in a standard 100 microliter ($\mu$l) PCR reaction which produced the expected 0.8 kilobase (kb) internal fragment of the malic enzyme gene. The PCR product was purified using a Qiaex Gel Extraction Kit (Qiagen, Inc., Chatsworth, Calif.) and biotinylated using a BioNick Labeling System (GibcoBRL, Gaithersburg, Md.). The biotinylated PCR product was used as the probe in the Southern Blot analysis of genomic E. coli DNA which had been cleaved with Hind III and one of several other second endonucleases. The malic enzyme gene was determined to be located in the region containing 2.0–2.5 kb fragments of Hind III and Pst I digested DNA.

Initial Malic Enzyme

Gene Cloning Detail

One microgram of E. coli DNA was digested with Hind III and Pst I and sized on a preparative 1 percent TAE agarose gel. The E. coli DNA fragments in the 2.0–2.5 kb region were isolated and purified using the Qiaex Gel Extraction Kit. The purified DNA fragments were ligated into the polylinker region of pUC19 which had been cleaved with Pst I and Hind III and treated with shrimp alkaline phosphatase. The ligated material was then used as a template for a PCR reaction to amplify the entire malic enzyme gene. One microliter of the ligation mixture was used as a template with 1 gM of sense primer GATGCCCCATG-GATATTCAAAAAAGAGTGAGT (*SEQ ID NO.3*), which targeted the malic enzyme gene, and 0.25 gM of antisense primer TTTTCCCAGTCACGACGTTG (*SEQ ID. NO.4*), which targeted the ligated pUC19 DNA. The amplification parameters were 94° C. denaturation, 55° C. hybridization for one minute and a 72° C. extension for three minutes for a total of 35 cycles. The PCR product was analyzed on a one percent TAE-agarose gel and the 1.8 kb fragment was isolated and purified using the Qiaex Gel Extraction Kit. A portion of the PCR product was digested with Bcl and Bgl to demonstrate that the product did contain the malic enzyme gene. The remainder of the PCR product was digested with Pst I and Nco I, gel isolated, repurified and then ligated into the polylinker region of the expression vector pTRC99a (Pharmacia, Piscataway, N.J.) which had been cleaved with Nco I and Pst I. E. coli strain NZN 111 was transformed with the ligation mixture by standard methods and the resulting colonies (four colonies from experimental and 2 colonies from control) were screened for the malic enzyme gene by restriction fragment analysis using Xmn (0.7 kb, 1.4 kb and 3.9 kb fragments expected). The plasmid containing the cloned malic enzyme gene was named pMEE3.

Alternative N-Terminus

Detail for Malic Enzyme

A 100 ml culture of NZN (pMEE3) was grown in an overnight culture and the plasmid was isolated using a Qiagen Plasmid Kit. The isolated plasmid was used as a template for PCR reaction. A new primer was designed to give an alternative N-terminus which was 81 base pairs down stream from the primer used in the first cloning of the malic enzyme. Twenty nanograms of plasmid was used as template with 1 $\mu$M of sense primer AGGATCCATGGAAC-CAAAAACAAAAAACC and (*SEQ ID. NO.5*) antisense primer CGCCAGGGTTTTCCCAGTCACGAC (*SEQ ID. NO.6*). The amplification parameters were the same as noted above. A portion of the PCR product was again verified by restriction mapping with Bcl I and Bgl II which verified that the product contained the malic enzyme gene. The remainder of the PCR material was digested with Pst I and Nco I and gel isolated, repurified and then ligated into the polylinker region of the expression vector PTrc99aa (Pharmacia, Inc. Piscataway, N.J.) which had been cleaved with Nco I and PSt I. E. coli strain JM109 was transformed with the ligation mixture by standard methods and the resulting colonies (three experimental clones and 1 control clone) were screened for the desired insert by restriction fragment analysis. The plasmid containing this version of the malic enzyme gene was named pMEE2.

Optimization of Promoter

Inducer Conditions Detail

Thirty milliliters of LB broth containing 100 μg/ml ampicillin were inoculated with 1.5 mls of an overnight culture of pMEE2. After two hours of growth, the 30 ml culture was separated into 3–10 ml aliquots. Enzyme activity was induced with 0, 100 μM, and 10 μM isopropylthiogalactoside (IPTG). A 2 ml sample was removed from each culture at 0, 1, 2, 3, and 4 hours. Protein was isolated according to standard methods and the activity was determined as noted above.

Enzyme production, over time is depicted in Table 2 below:

TABLE 2

Malic enzyme production induced by IPTG in LB broth.

| Time (hour) | Without IPTG | 100 μM IPTG | 10 μ IPTG |
|---|---|---|---|
| | μg/min/mg protein | | |
| 0 | 3.09 | — | — |
| 1 | 4.83 | 26.5 | 5.84 |
| 2 | 4.26 | 38.2 | 10.06 |
| 3 | 8.46 | 75.3 | 32.7 |
| 4 | 9.92 | 88.2 | 38.95 |

Figure 2:
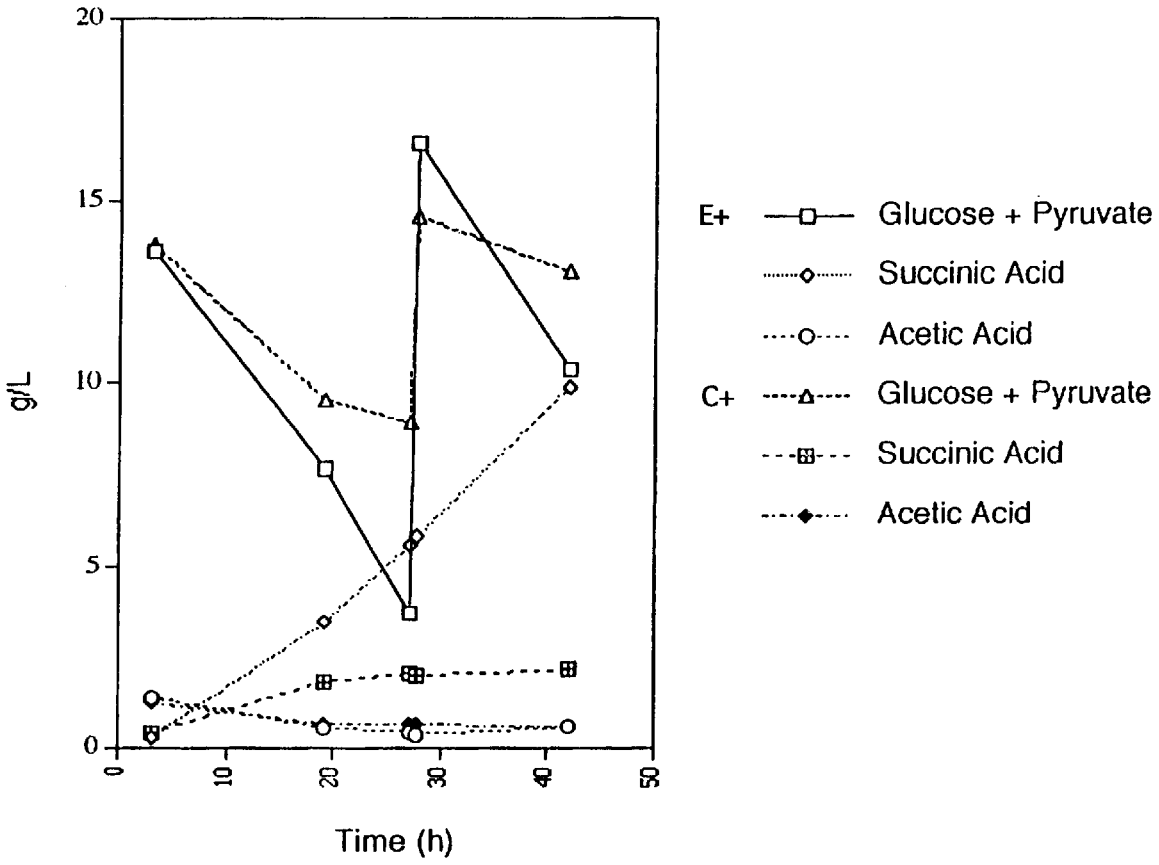
FIG. 2 is a graph depicting an enhanced production of succinic acid after transformation of NZN 111 with malic enzyme gene, in accordance with the present invention.

The physiological effect of pMEE2 expression is depicted in FIG. 2. Duplicate cultures of NZN 111(pMEE2) and, as a control, NZN 111(pTRC99a) were grown aerobically in 2 ml LB medium containing ampicillin. One culture of each was induced with 10 μM IPTG. After three hours, $OD_{600}$ had increased from 0.6 to 4.8. One milliliter of the cultures were injected into sealed 58 ml vials containing 10 ml of LB medium containing glucose at 20 g/L, acetate at 1 g/L and 0.5 g of solid $MgCO_3$. The atmosphere consisted of air:hydrogen:carbon dioxide in a 1:1:2 ratio at 1 atm pressure above ambient pressure. The culture was sampled immediately and at intervals during incubation at 37° C. with shaking at 100 rpm. Table 3 below provides a comparison of product yields when NZN 111 is transformed with raw vector (pTRC99a) versus pMEEb 2.

TABLE 3

Effect of expression of malic enzyme in NZN 111 (pMEE2) versus NZN 111 (pTRC99a)

| Product | Vector | mae A |
|---|---|---|
| | g/L | |
| Succinic Acid | 0.3 | 6.5 |
| Lactic Acid | 0.4 | 0.4 |
| Acetic Acid | 0 | 0 |
| Ethanol | 0 | 0.2 |

The results depicted in Table 3 are the result of incubation periods of between approximately 19 and 42 hours.

Lactobacillus Mutant Detail

The inventors also have determined a method for higher production of malic acid via fermentation. Malic acid, a precursor of succinic acid is in principle a better end product than succinic acid, in as much as its production requires one less reductive step. The theoretical stoichiometry for malic acid production is one mole of glucose and two moles of carbon dioxide converted to two moles of malic acid. As such, the production of malic acid could occur without waste of glucose. Fumaric acid, which is the dehydration product of malic acid and the precursor of succinate in the reduction pathway, could also be formed. Both malic acid and fumaric acid also could be formed without the production of co-product, but the higher solubility of malic acid makes it preferable for large scale production processes.

The transformation of suitable bacteria with a gene responsible for production of malic enzyme (such as maeA) could result in a surplus of malate. Generally, the ideal bacteria would lack lactate dehydrogenase activity, and other enzymes which metabolize pyruvate, thereby resulting in an accumulation of pyruvate. The bacteria are instead transformed with maeA to directly produce malate. To maintain the high levels of malate produced, the bacteria must not be capable of converting the malate back to lactate, or on to fumarate or succinate. In as much as some Lactobacillus strains lack the malolactate enzyme, fumarase, and fumarate reductase responsible for such conversions, this strains are particularly suitable candidates for malate production in fermentation processes. The suitability of Lactobacillus is further enhanced given its very high osmotolerant characteristics. Lactobacillus gasseri is a near term host for such manipulation since it has been shown not to metabolize malate during the fermentation of glucose and is fairly well characterized genetically. Lactobacillus casei also holds considerable potential in as much as it exhibits relatively higher osmotolerance than L. gasseri.

Generally, a malic enzyme gene (such as maeA) in a suitable lactobacillus expression vector, such as pTRK327 induced in a lactobacillus host lacking a functional lactate dehydrogenase gene, would allow formation of malic acid. This could be achieved by insertion of the malic enzyme into the host's lactate dehydrogenase gene.

While the invention has been described with reference to details of the illustrated embodiment, these details are not intended to limit the scope of the invention as defined in the appended claims.

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
(A) LENGTH: 23 bases
(B) TYPE: nucleic acid
(C) STRANDEDNESS: Not Applicable
(D) TOPOLOGY: linear (ii) MOLECULE TYPE:Genomic DNA (iii) HYPOTHETICAL: yes (xi) SEQUENCE DESCRIPTION: SEQ ID NO: 1:

CGAAGAACAA GCGGAACGAG CAT 23

(2) INFORMATION FOR SEQ ID NO: 2:

(i) SEQUENCE CHARACTERISTICS:
(A) LENGTH: 23 bases
(B) TYPE: nucleic acid
(C) STRANDEDNESS: Not Applicable
(D) TOPOLOGY: linear (ii) MOLECULE TYPE:Genomic DNA (iii) HYPOTHETICAL: yes (xi) SEQUENCE DESCRIPTION: SEQ ID NO: 2:

GGCAGCAGGT TCGGCATCTT GTC 23

(2) INFORMATION FOR SEQ ID NO: 3:

(i) SEQUENCE CHARACTERISTICS:
(A) LENGTH: 32 bases
(B) TYPE: nucleic acid
(C) STRANDEDNESS: Not Applicable
(D) TOPOLOGY: linear (ii) MOLECULE TYPE:Genomic DNA (iii) HYPOTHETICAL: yes (xi) SEQUENCE DESCRIPTION: SEQ ID NO: 3:

GATGCCCCAT GGATATTCAA AAAAGAGTGA GT 32

(2) INFORMATION FOR SEQ ID NO: 4:

(i) SEQUENCE CHARACTERISTICS:
(A) LENGTH: 20 bases
(B) TYPE: nucleic acid
(C) STRANDEDNESS: Not Applicable
(D) TOPOLOGY: linear (ii) MOLECULE TYPE:Genomic DNA (iii) HYPOTHETICAL: yes (xi) SEQUENCE DESCRIPTION: SEQ ID NO: 4:

TTTTCCCAGT CACGACGTTG 20

(2) INFORMATION FOR SEQ ID NO: 5:

(i) SEQUENCE CHARACTERISTICS:

-continued

```
          (A) LENGTH: 28 bases
          (B) TYPE:  nucleic acid
          (C) STRANDEDNESS: Not Applicable
          (D) TOPOLOGY: linear

    (ii) MOLECULE TYPE:Genomic DNA

   (iii) HYPOTHETICAL: yes

    (xi) SEQUENCE DESCRIPTION: SEQ ID NO: 5:

AGGATCCATG GAACCAAAAA CAAAAAAC                                    28


(2) INFORMATION FOR SEQ ID NO: 6:

     (i) SEQUENCE CHARACTERISTICS:
          (A) LENGTH: 24 bases
          (B) TYPE:  nucleic acid
          (C) STRANDEDNESS: Not Applicable
          (D) TOPOLOGY: linear

    (ii) MOLECULE TYPE:Genomic DNA

   (iii) HYPOTHETICAL: yes

    (xi) SEQUENCE DESCRIPTION: SEQ ID NO: 6:

CGCCAGGGTT TTCCCAGTCA CGAC                                        24
```

The embodiment of the invention in which an exclusive property or privilege is claimed is defined as follows:

1. A method for isolating succinic acid producing bacteria comprising:

a.) isolating a facultative organism lacking the capacity to catabolize pyruvate *under fermentative conditions*;

b.) increasing the biomass of the organism in an aerobic process;

c.) subjecting the biomass to glucose-rich medium in an anaerobic environment to enable pyruvate-catabolizing mutants to grow; and d.) isolating a mutant characterized in that it produces a mixture of succinic acid, acetic acid and ethanol as fermentation products, which has been derived from a parent which lacked the genes for pyruvate formate lyase and lactate dehydrogenase which belongs to the E. coli Group of Bacteria.

2. The method as recited in claim 1 wherein the facultative organism lacks pyruvate formate lyase and lactate dehydrogenase activity.

3. The method as recited in claim 1 wherein the facultative organism lacking the capacity to catabolize pyruvate is NZN 111.

4. The method as recited in claim 1 wherein the organism is cultured aerobically on Luria broth.

5. The method as recited in claim 1 wherein the biomass is increased to between approximately $10^9$ to $10^{10}$ cells per milliliter.

6. The method as recited in claim 1 wherein the glucose-rich medium contains between approximately 1 g/l and 30 g/l of glucose.

7. A mutant characterized in that it produces a mixture of succinic acid, acetic acid and ethanol as fermentation products, which has been derived from a parent which lacked the genes for pyruvate formate lyase and lactate dehydrogenase which belongs to the E. coli Group of Bacteria.

8. A mutant as described in claim 7 wherein the parent is NZN 111.

9. AFP 111, as claimed in claim 7.

10. A mutant as described in claim 7 wherein succinic acid is the major fermentation product.

* * * * *